United States Patent
Sharma et al.

(10) Patent No.: US 11,386,537 B2
(45) Date of Patent: Jul. 12, 2022

(54) ABNORMALITY DETECTION WITHIN A DEFINED AREA

(71) Applicant: Shanghai United Imaging Intelligence Co., LTD., Shanghai (CN)

(72) Inventors: Abhishek Sharma, Cambridge, MA (US); Meng Zheng, Troy, NY (US); Srikrishna Karanam, Cambridge, MA (US); Ziyan Wu, Cambridge, MA (US); Arun Innanje, Cambridge, MA (US); Terrence Chen, Cambridge, MA (US)

(73) Assignee: Shanghai United Imaging Intelligence Co., LTD., Shanghai (CN)

( * ) Notice: Subject to any disclaimer, the term of this patent is extended or adjusted under 35 U.S.C. 154(b) by 323 days.

(21) Appl. No.: 16/802,989

(22) Filed: Feb. 27, 2020

(65) Prior Publication Data

US 2021/0272258 A1    Sep. 2, 2021

(51) Int. Cl.
| | | |
|---|---|---|
| *G06T 7/00* | (2017.01) | |
| *G16H 40/67* | (2018.01) | |
| *G06N 20/10* | (2019.01) | |
| *G06F 17/18* | (2006.01) | |
| *G06N 3/08* | (2006.01) | |
| *G06N 5/04* | (2006.01) | |

(52) U.S. Cl.
CPC ............ *G06T 7/0002* (2013.01); *G06F 17/18* (2013.01); *G06N 3/084* (2013.01); *G06N 3/088* (2013.01); *G06N 5/04* (2013.01); *G06N 20/10* (2019.01); *G06T 7/97* (2017.01); *G16H 40/67* (2018.01); *G06T 2207/20076* (2013.01); *G06T 2207/20081* (2013.01); *G06T 2207/20084* (2013.01)

(58) Field of Classification Search
CPC ...... G06N 20/10; G06N 3/0454; G06N 3/084; G06N 3/088; G06N 5/04; G06T 2207/20081; G06T 2207/20084; G06T 7/0002; G06V 10/82
See application file for complete search history.

(56) References Cited

U.S. PATENT DOCUMENTS

| | | | |
|---|---|---|---|
| 2019/0304099 A1* | 10/2019 | Hever | G06K 9/6274 |
| 2021/0065440 A1* | 3/2021 | Sunkavalli | G06N 3/08 |
| 2021/0080531 A1* | 3/2021 | Gui | G01R 33/543 |

* cited by examiner

*Primary Examiner* — Ruiping Li
(74) *Attorney, Agent, or Firm* — Ziegler IP Law Group, LLC (57) ABSTRACT

Abnormality detection within a defined area includes obtaining a plurality of images of the defined area from image-capture devices. An extent of deviation of one or more types of products from an inference of each of the plurality of images is determined using a trained neural network. A localized dimensional representation is generated in a portion of an input image associated with a first location of the plurality of locations, based on gradients computed from the determined extent of deviation. The generated localized dimensional representation provides a visual indication of an abnormality located in the first location within the defined area. An action associated with the first location is executed based on the generated dimensional representation for proactive control or prevention of occurrence of undesired event in the defined area.

20 Claims, 8 Drawing Sheets

FIG. 5C

ABNORMALITY DETECTION WITHIN A DEFINED AREA

FIELD

The aspects of the disclosed embodiments relate generally to abnormality detection systems, and more particularly to abnormality detection within a defined area, such as a hospital environment or room.

BACKGROUND

In certain environments, such as a hospital, protocols and procedures are followed for safety measures. For example, carrying metal objects inside a medical scanning facility, in which an imaging device, such as a Medical Resonance Imaging (MRI) device or a Computed Tomography (CT) device, is an undesirable event. Video surveillance of such environments (e.g. hospital environment) is typically performed using closed-circuit television (CCTV). However, such conventional video surveillance is a tedious task, error-prone, and not full-proof. Undesirable events in such environments may be overlooked or go undetected.

Certain attempts have been made to develop surveillance systems employing machine learning techniques. However, there are many technical problems in such conventional systems. The conventional systems are computational resource intensive (i.e. memory and computational power intensive) and are usually inaccurate. As an example, conventional systems may require separate neural networks for individual tasks (e.g. one neural network may be used for an image processing/encoding task and another for a visualization task). By virtue of using separate neural networks, more training data and time is required to train separate neural networks. System complexity and the chances of inaccuracy increases, which is not desirable.

Accordingly, it would be desirable to provide methods and apparatus that address at least some of the problems described above.

SUMMARY

The aspects of the disclosed embodiments are directed to a method and system for abnormality detection within a defined area. This and other advantages of the disclosed embodiments are provided substantially as shown in, and/or described in connection with, at least one of the figures, as set forth in the independent claims. Further advantageous modifications can be found in the dependent claims.

According to a first aspect, the disclosed embodiments provide a method for abnormality detection within a defined area, the method including:
  obtaining, by a processor, a plurality of images of the defined area from one or more image-capture devices;
  computing, by the processor using a trained neural network, one or more products from an inference with each input image of the plurality of images, wherein the plurality of images are associated with a plurality of different locations in the defined area;
  determining, by the processor using the trained neural network, an extent of deviation of properties of a probability distribution of each input image of the plurality of images with respect to a referential probability distribution of one or more reference images;
  computing by the processor using the trained neural network, gradients associated with the trained neural network based on at least the determined extent of deviation for at least one input image of the plurality of images when the determined extent of deviation for the at least one input image is greater than a defined threshold;
  generating, by the processor using the trained neural network, a localized two-dimensional or three-dimensional representation in a portion of the at least one input image associated with a first location of the plurality of locations, based on the computed gradients, wherein the generated localized two-dimensional or three-dimensional representation provides a visual indication of an abnormality located in the first location within the defined area; and
  executing, by the processor, an action associated the first location in the defined area based on the generated localized two-dimensional or three-dimensional representation, wherein the executed action causes a proactive control of an occurrence of an undesired event in the defined area.

According to a second aspect the disclosed embodiments provide a system for abnormality detection within a defined area, the system including:
  a server that includes a processor configured to:
    obtain a plurality of images of the defined area from one or more image-capture devices;
    compute, using a trained neural network, one or more types of products from an inference with each input image of the plurality of images, wherein the plurality of images are associated with a plurality of different locations in the defined physical area;
    determine, using the trained neural network, an extent of deviation of properties of a probability distribution of each input image of the plurality of images with respect to a referential probability distribution of one or more reference images;
    compute, using the trained neural network, gradients associated with the trained neural network based on at least the determined extent of deviation for at least one input image of the plurality of images when the determined extent of deviation for the at least one input image is greater than a defined threshold;
    generate, using the trained neural network, a localized two-dimensional or three-dimensional representation in a portion of the at least one input image associated with a first location of the plurality of locations, based on the computed gradients, wherein the generated localized two-dimensional or three-dimensional representation provides a visual indication of an abnormality located in the first location within the defined area; and
    execute an action associated the first location in the defined area based on the generated localized two-dimensional or three-dimensional representation, wherein the executed action causes a proactive control of an occurrence of an undesired event in the defined area.

According to a third aspect the disclosed embodiments provide a non-transitory computer-readable medium having stored thereon, computer implemented instructions that when executed by a computer cause the computer to execute operations, the operations including:
  obtaining a plurality of images of a defined area from one or more image-capture devices;
  computing, using a trained neural network, one or more types of products from an inference with each input image of the plurality of images, wherein the plurality of images are associated with a plurality of different locations in the defined area;

determining, using the trained neural network, an extent of deviation of properties of a probability distribution of each input image of the plurality of images with respect to a referential probability distribution of one or more reference images;

computing, using the trained neural network, gradients associated with the trained neural network based on at least the determined extent of deviation for at least one input image of the plurality of images when the determined extent of deviation for the at least one input image is greater than a defined threshold;

generating, using the trained neural network, a localized two-dimensional or three-dimensional representation in a portion of the at least one input image associated with a first location of the plurality of locations, based on the computed gradients, wherein the generated localized two-dimensional or three-dimensional representation provides a visual indication of an abnormality located in the first location within the defined area; and executing an action associated the first location in the defined area based on the generated localized two-dimensional or three-dimensional representation, wherein the executed action causes a proactive of an occurrence of an undesired event in the defined area.

The aspects of the disclosed embodiments enable an accurate, computational power efficient, and memory efficient identification of abnormalities in environments, such as a hospital environment, in real time or near-real time. The various aspects of the disclosed embodiments not only ensure identification of abnormalities in these environments but also execute an action. An example of such an action can include, but is not limited to, for example, outputting an alert together with visual information to indicate or pinpoint the abnormality located in a specific location within the environment, also referred to herein as a defined area or defined physical area. The visual information provides a visual explanation indicative of a reason of the alert. The executed action ensures a proactive control or even the prevention of an occurrence of an undesired event in the defined area.

These and other aspects, implementation forms, and advantages of the exemplary embodiments will become apparent from the embodiments described herein considered in conjunction with the accompanying drawings. It is to be understood, however, that the description and drawings are designed solely for purposes of illustration and not as a definition of the limits of the disclosed invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

In the following detailed portion of the present disclosure, the invention will be explained in more detail with reference to the example embodiments shown in the drawings, in which.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF THE DISCLOSED EMBODIMENTS

The following detailed description illustrates exemplary aspects of the disclosed embodiments and ways in which they can be implemented. Although some modes of carrying out the aspects of the disclosed embodiments have been disclosed, those skilled in the art would recognize that other embodiments for carrying out or practising the aspects of the disclosed embodiments are also possible.

The aspects of the disclosed embodiments are directed to providing a method and system for accurate abnormality detection or identification in a defined area or environment, such as a hospital environment. In some conventional systems and methods, multiple neural networks are used, usually one for image processing task and another for visualization task. Further, some conventional systems and methods produce heatmaps using a separate neural network based on certain scoring mechanism to visualize different regions responsible for the abnormality. However, such conventional systems are computational resource intensive, requiring large amounts of computations and memory space.

In contradiction to conventional systems and methods, various aspects of the disclosed system and methods are computational resource efficient, as a same neural network is used to perform the image processing and visualization task in a more accurate manner. This reduces the system complexity as separate training data is not required to train for visualization. Moreover, various aspects of the disclosed system and methods enables to generate a localized two-dimensional or three-dimensional representation which may be referred to as an attention map, in a localized portion of an input image to indicate abnormality in a defined area, such as a hospital environment. Alternatively stated, an attention-based mechanism is used by the neural network, such as a variational autoencoder, for example, to accurately and quickly detect and then localize abnormalities in the input image, which can be a scene of a hospital environment, for example.

Figure 1:
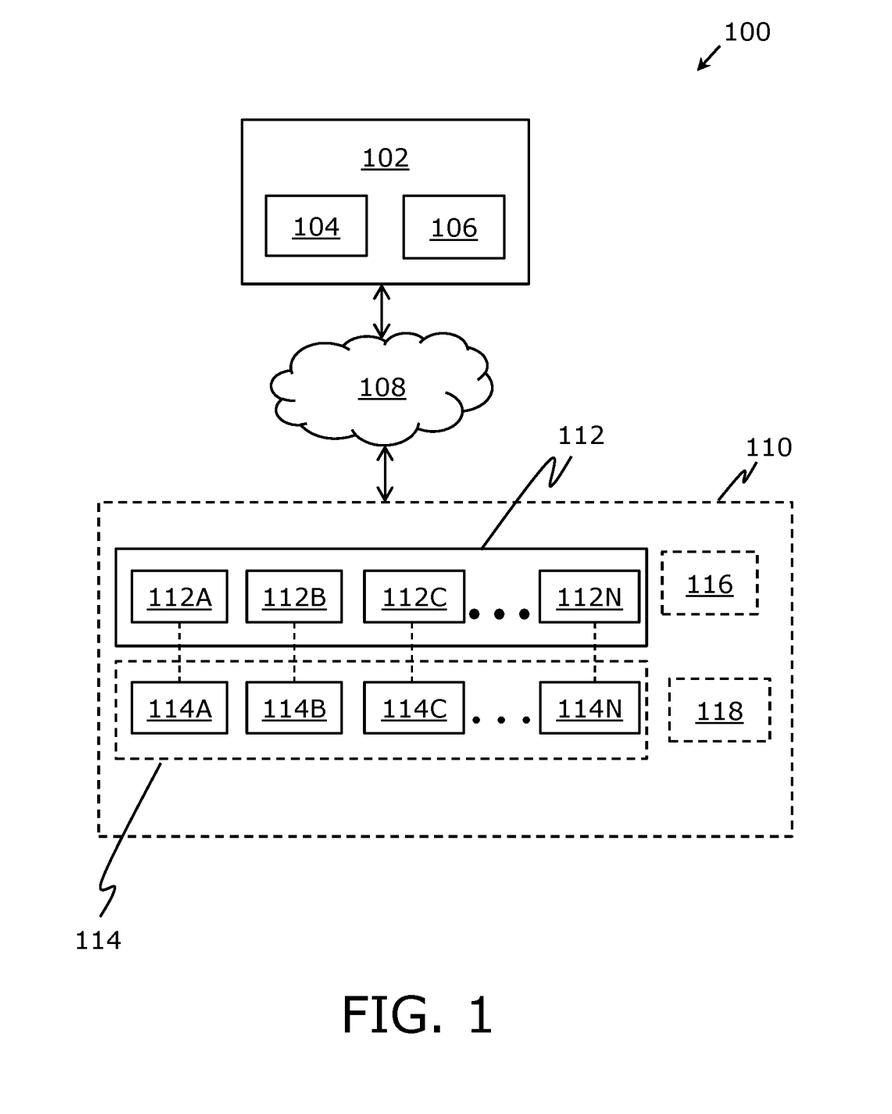
FIG. 1 is a network environment diagram of an exemplary system for abnormality detection within a defined area, in accordance with the aspects of the disclosed embodiments.

FIG. 1 is a network environment diagram of an exemplary system for abnormality detection within a defined area in accordance with the aspects of the disclosed embodiments. With reference to FIG. 1, there is shown a network environment diagram of a system 100 that includes a server 102.

The server 102 includes a processor 104 and an neural network 106. There is further shown a communication network 108, a defined area 110, one or more image-capture devices 112, and a plurality of different locations 114. The image-capture devices 112 (namely a first image-capture device 112A, a second image-capture device 112B, a third image-capture device 112C, and an Nth image-capture device 112N) are installed in the defined area 110 or in a manner that the image capture devices 112 can capture images of the defined area 110. Each of the image-capture devices 112 is installed (or placed) with respect to a specific location of the plurality of different locations 114 within the defined area 110.

For example, the first image-capture device 112A is provided at a first location 114A. Similarly, the second image-capture device 112B, the third image-capture device 112C, and the Nth image-capture device 112N is provided at a second location 114B, a third location 114C, and an Nth location 114N respectively (as shown). The server 102 is communicatively coupled to the image-capture devices 112 via the communication network 108. Optionally, a medical equipment or device 116 and a plurality of medical imaging devices 118 are communicatively coupled to the server 102.

The server 102 includes suitable logic, circuitry, interfaces and/or code that is configured to receive a plurality of images of the defined area 110 from the one or more image-capture devices 112. In some embodiments, the server 102 is potentially configured to receive a sequence of image frames (e.g. one or more video) of the defined area 110 from the plurality of image-capture devices 112. Examples of the server 102 may include, but are not limited to, an application server, a web server, a database server, a file server, a cloud server, or a combination thereof.

The processor 104 includes suitable logic, circuitry, interfaces and/or code that is configured to process the plurality of images (or the sequence of image frames) by use of the neural network 106. The processor 104 is configured to respond to and process instructions that drive the system 100. Examples of the processor 104 includes, but is not limited to, a microprocessor, a microcontroller, a complex instruction set computing (CISC) microprocessor, a reduced instruction set (RISC) microprocessor, a very long instruction word (VLIW) microprocessor, or any other type of processing circuit. Optionally, the processor 104 may be one or more individual processors, processing devices and various elements associated with a processing device that may be shared by other processing devices. Additionally, the one or more individual processors, processing devices and elements are arranged in various architectures for responding to and processing the instructions that drive the system 100.

The neural network 106 refers to an artificial neural network configured to receive an input, compress the input, and decompress the compressed input to generate an output such that the generated output is similar to the received input. Alternatively stated, the neural network 106 is used to reduce the size of input data into a smaller representation, and whenever original data is needed, it can be reconstructed from the compressed data. One example of such a neural network 106 is a variational autoencoder.

As an example, the neural network 106 may include an encoder that compresses the input having an initial space into a latent space, and a decoder that decompress the encoded input. In an implementation, the neural network 106 is an unsupervised neural network that uses machine learning to do the compression. The neural network 106 is configured to detect abnormalities in the plurality of different locations 114 based on the input of the plurality of images that are associated with the plurality of different locations 114 in the defined area 110.

In one embodiment, the neural network 106 is a variational autoencoder. The variational autoencoder is an autoencoder trained in a way that the latent space is regularized. In comparison to typical autoencoders, instead of encoding the input as a single point, the input is encoded as a distribution over the latent space by the variational autoencoders.

In another embodiment, the neural network 106 is an attention-based variational autoencoder. In this embodiment, the neural network 106 is able to generate an attention map along with de-compressed input as an output. For example, a single neural network is able to perform both image processing/encoding tasks and visualization tasks. A separate network is not required to generate visualization, such as a localized two-dimensional representation, also referred to as attention map, in an image or a sequence of images, such as a video.

The communication network 108 includes a medium through which the plurality of image-capture devices 112 and the server 102 communicate with each other. The communication network 108 may be a wired or wireless communication network. Examples of the communication network 108 may include, but are not limited to, a Wireless Fidelity (Wi-Fi) network, a Local Area Network (LAN), a wireless personal area network (WPAN), a Wireless Local Area Network (WLAN), a wireless wide area network (WWAN), a cloud network, a Long Term Evolution (LTE) network, a plain old telephone service (POTS), a Metropolitan Area Network (MAN), and/or the Internet. The plurality of image-capture devices 112 are potentially configured to connect to the communication network 108, in accordance with various wired and wireless communication protocols. Examples of such wired and wireless communication protocols may include, but are not limited to, Transmission Control Protocol and Internet Protocol (TCP/IP), User Datagram Protocol (UDP), Hypertext Transfer Protocol (HTTP), File Transfer Protocol (FTP), ZigBee, EDGE, infrared (IR), IEEE 802.11, 802.16, Long Term Evolution (LTE), Light Fidelity (Li-Fi), and/or other cellular communication protocols or Bluetooth (BT) communication protocols, including variants thereof.

The defined area 110 refers to an environment or physical space, also referred to as an operating environment, such as a hospital environment. In an example, the defined area 110 may include one or more robots/machines which perform a specific task at the defined area 110 based on a defined set of protocols and procedures. As an example, the plurality of different locations 114 in the hospital environment may include, but are not limited to, a magnetic resonance imaging (MRI) room, a computed tomography (CT) room, operation theatres, hallways, restricted sections in the hospital environment and the like. In these example, one or more robots may perform one or more tasks in the magnetic resonance imaging (MRI) room. In another example, the defined area 110 may be a factory, an office building, an industrial complex, and the like.

Each of the one or more image-capture devices 112 includes suitable logic, circuitry, interfaces and/or code that is configured to capture a plurality of images of the defined area 110 at the plurality of different locations 114. Optionally, the plurality of images captured by the image-capture devices 112 may be moving images, still images or a combination thereof. In an implementation, the plurality of images is of a hospital environment. Examples of each of the image-capture devices 112 include, but are not limited to a digital camera, an image sensor, night vision capable camera, a video recorder, a CCTV camera, and other type of image-capture devices.

In one aspect, the disclosed embodiments include a training phase and an operational phase. In the training phase, the neural network 106 is trained, using training data, to enable the neural network 106 to perform specific intended functions in the operational phase. The processor 104 is configured to execute an unsupervised or a semi-supervised training of the neural network 106 using training data of images of the defined physical area 110 to obtain a trained neural network 106. In the unsupervised training of the neural network 106, unlabeled training data is used for training of the neural network 106. Moreover, in the semi-supervised training of the neural network 106, a comparatively small amount of labeled training data and a large amount of unlabeled training data is used for training of the neural network 106.

As an example, while training of neural network 106, images, for example normal 2D images, of the defined area 110 and some images with abnormality are fed to the neural network 106. Initially, the neural network 106 is potentially not provided with information about where the abnormality is present in the images having abnormality. The neural network 106 automatically finds the abnormality in the images. The term "abnormality" refers to deviation in following the defined set of protocols and procedures while performing a specific task. For example, in an image a robot may be detected at a location which may be not its designated storage or usage location.

In accordance with an embodiment, the training data includes images, or a sequence of images, provided by the plurality of image-capture devices to the server 102. Optionally, the training data of images of the defined physical area 110 is pre-stored in the server 102. Based on the training of the neural network 106, a trained neural network 106 is obtained which is used in the operational stage of the system 100.

In operation, the processor 104 is configured to obtain a plurality of images of the defined area 110 from the plurality of image-capture devices 112. The processor 104 receives the plurality of images via the communication network 108. The plurality of images is obtained in real time or near-real time as such images are captured. Optionally, each of the plurality of images has a time stamp associated therewith. In an embodiment, the server 102 is configured to store information about a location associated with each of the plurality of image-capture devices 112. Thus, when one or more images from a specific image-capture device of the plurality of image-capture devices 112 is received, the processor 104 associated the location of the specific image-capture device with the one or more images captured by the specific image-capture device. The processor 104 is configured to store the received plurality of images in the server 102, such as the memory of the server 102.

The processor 104 is further configured to compute, using the trained neural network 106, one or more types of products from an inference with each input image. Examples of one or more types of products can include, but are not limited to, properties of probability distribution like mean and standard deviation vectors. Another example of one or more types of product of inference can be gradients of some layer in the neural network The trained neural network 106 is configured to receive each image of the plurality of images as an input and further process the input to generate the one or more types of products from an inference, such as the mean vector and the standard deviation vector. For example, the encoder of the neural network 106 is configured to compute the mean vector and the standard deviation vector of each input image. The mean vector generally represents where the encoding of the input should be centered around. The standard deviation vector generally represents an extent up to which the encoding may vary from the mean vector.

As an example, the neural network 106 is configured to employ a probability distribution on parameters. such as applied on pixels, of each input image to compute a mean vector and a standard deviation vector of each input image. Optionally, the processor 104, using the trained neural network 106, is configured to compute the mean vector and the standard deviation vector based on the training received in the training phase. Optionally, the computed mean vector and the standard deviation vector are numerical values.

In accordance with an embodiment, the processor 104 is further configured to determine an extent of deviation of properties of a probability distribution of each input image of the plurality of images with respect to a referential probability distribution of one or more reference images. In one embodiment, this includes comparing the computed mean vector and the standard deviation vector of each input image of the plurality of images with a reference mean vector and a reference standard deviation vector of a reference image to determine an extent of deviation. In other words, the values of the computed mean vector and the standard deviation vector of each input image is compared with the corresponding values of the reference mean vector and the reference standard deviation vector. The information of reference mean vector and the reference standard deviation vector of each reference image is pre-stored in the server 102.

As an example, such information corresponds to actual mean vector and standard deviation vectors obtained at the time of training phase, and are potentially validated information. The processor 104 is configured to determine a difference between the computed mean vector and the reference mean vector, and a difference between the computed standard deviation vector and the reference standard deviation vector based on the comparison.

The processor 104 is further configured to determine, using the trained neural network 106, an extent of deviation of properties of a probability distribution of each input image of the plurality of images with respect to a referential probability distribution of one or more reference images. In one embodiment, this can include determining the computed mean vector and the standard deviation vector of each input image of the plurality of images with respect to the reference mean vector and the reference standard deviation vector of a reference image. Notably, after the training of the neural network 106, references images are stored in the server 102 along with the information of the reference mean vector and the reference standard deviation vector of each reference image.

As an example, the reference image of a given location may represent an image of a location having no abnormality. For example, a robot in a surgery room of the hospital environment is configured to perform an operation following a defined protocol. In such an example, an image, or a sequence of images, that includes the robot performing the operation following the defined protocol may be used the reference image. The term "extent of deviation" refers to an amount of variation in properties of a probability distribution of each input image of the plurality of images with respect to a referential probability distribution of one or more reference images. This can include an amount of variation of the computed mean vector of a given input image with respect to a reference mean vector of a given reference image and an amount of variation in the computed standard deviation vector of the given input image with respect to a reference standard deviation vector of the given reference image.

As an example, the reference image is selected is similar to the input image. In another example, the selected reference image may not be similar to the input image.

In accordance with an embodiment, the processor 104 is further configured to derive, using the trained neural network 106, resultant vectors for the at least one input image of the plurality of images, where the resultant vectors are derived from a difference of the computed mean vector and the standard deviation vector of the at least one input image from the reference mean vector and the reference standard deviation vector. The resultant vectors are derived based on the comparison performed, by the processor 104, between the computed mean vector and the standard deviation vector of the at least one input image from the reference mean vector and the reference standard deviation vector.

For example, by subtracting the computed mean vector and the standard deviation vector of the at least one input image from the reference mean vector and the reference standard deviation vector, the resultant vectors may be obtained. Further, the resultant vectors are used by a decoder of the trained neural network 106. Optionally, the resultant vectors may also be referred as latent vectors.

The processor 104 is further configured to compute, using the trained neural network 106, gradients associated with the trained neural network 106 based on at least the determined extent of deviation for at least one input image of the plurality of images when the determined extent of deviation for the at least one input image is greater than a defined threshold. In an embodiment, the processor 104 is further configured to apply backpropagation by use of the resultant vectors in the trained neural network to compute the gradients. Notably the neural network 106 is configured to have a plurality of layers. In backpropagation, a gradient of a given layer of the plurality of layers is calculated based on a previous layer, thereby forming a chain. As the gradient of a layer depends on a gradient of a previous layer, the gradient is determined backwards. Typically, the backpropagation is employed to reduce any errors in the output that is to be subsequently produced by the decoder of the trained neural network 106.

Optionally, the extent of deviation has a value greater than a threshold value (i.e. the defined threshold). Optionally, in an example, the gradients may be calculated by using the extent of deviation with respect to feature action maps of convolution layers of the encoder of the neural network 106. These gradients flowing back are global average polled over height and width to obtain the importance weights. Optionally, in another example, to compute the gradients, certain Gradients computation algorithms, such as a Gradient descent algorithm, may be used by the trained neural network 106. The defined threshold may be pre-defined or set in real time or near real time.

The processor 104 is configured to generate, using the neural network 106, a localized dimensional representation in a portion of the at least one input image associated with a first location (e.g. the first location 114A) of the plurality of different locations 114, based on the computed gradients. The dimensional representation can include one or more of a two-dimensional representation or a three-dimensional representation. The generated localized dimensional representation provides a visual indication of an abnormality located in the first location within the defined area 110.

The localized two-dimensional or three-dimensional representation may also be referred to as a localized attention map. Moreover, the aforesaid portion of the at least one input image refers to a region in the input image that potentially includes an object that exhibits some form of abnormality. The term "abnormality" refers to any deviation in the specific task performed at the plurality of different locations 114 such that the deviation may result in any undesirable incident. In other words, abnormality refers to deviation in following the defined set of protocols and procedures while performing the specific task.

As an example, in a hospital environment a person using a metal object in a medical scanning room such as MRI room is considered as an abnormality. In another example, in a hospital environment some robots performing abnormal actions in a surgery room is considered as an abnormality. As the input image in which the abnormality is detected is associated with the first location, a precise localization (i.e. pinpointing) of the abnormality in the entire hospital environment (i.e. the defined area 110) is achieved.

Moreover, the generated localized two-dimensional representation provides a visual explanation which not only highlights the abnormality located in the first location, but also provides a visual explanation as to why the portion of the input image associated with the first location is considered as abnormal. This increases the confidence to accept and proactively act on the detected abnormality. As a result, identification of a location of abnormality in the first location becomes easier using the generated localized two-dimensional or three-dimensional representation.

Beneficially, according to the aspects of the disclosed embodiments, a localized two-dimensional or three-dimensional representation is made only in a specific portion of the at least one input image, in comparison to conventional technologies that use heat maps to classify objects (or areas) over the whole image. This further reduces the use of computational resources. For example, comparatively less memory space is required, while the accuracy in the detection of the abnormality is increased.

As an example, in a hospital environment, the input image of the MRI room may have a localized two-dimensional representation of the portion of the input image depicting a metal object carried by a patient. Optionally, a linear combination of obtained importance weights with activation maps of the convolution layers are used to obtain the localized two-dimensional or three-dimensional representation.

Notably, generation of a localized two-dimensional or three-dimensional representation based on the computed gradients is advantageous as then two separate neural networks, or multiple neural networks or complex systems, are not required to generate the visualization. In contradiction to conventional systems and methods, as a same neural network (e.g. the neural network 106) is used to perform the image processing and visualization task in a more accurate manner, the system complexity is reduced.

The processor 104 is further configured to execute an action associated with the first location, such as first location 114A, in the defined area 110 based on the generated localized two-dimensional or three-dimensional representation. The executed action can include or cause a proactive control or prevention of an occurrence of an undesired event in the defined area 110. Optionally, the action is executed by transmitting signals and/or information of the abnormality to one or more entities associated with defined area 110.

In one embodiment, the processor 104 is configured to communicate an alert together with visual information, to a specified electronic device, such as a smartphone or other portable device, that is mapped or otherwise communicatively coupled to a user present in the defined area 110. The alert is communicated based on the generated localized two-dimensional or three-dimensional representation to indicate the abnormality located in the first location within the defined area 110. The visual information is a visual explanation indicative of a reason of the alert. The alert together with visual information is communicated as a part of the action associated the first location in the defined area 110.

As an example, in a hospital environment, the processor 104 communicates the alert together with visual information to a smartphone of a hospital personnel, such as a doctor or a lab assistant. The hospital personnel may be associated with a specific location, such as an MRI room, in case the abnormality is detected in the MRI room.

As another example, in a hospital environment, the processor 104 communicates the alert together with visual information to a supervisor in the vicinity of the first location. Optionally, upon receiving the alert together with visual information the user of the specified electronic device is configured to act to proactively to control or prevent an occurrence of an undesired event. For example, in a hospital environment, upon receiving the alert, the doctor may ask a person carrying a metal object and moving towards an MRI room, to stop entering the room or may ask the person to leave the metal object outside the MRI room.

The electronic device may include, but is not limited to a cellular phone, personal digital assistants, handheld devices, wireless modems, laptop computers, personal computers and the like. The electronic devices can be mapped with registered users and communicatively coupled to the processor 104. In one embodiment, the processor 104 is configured to identify one or more electronic devices in the vicinity of the defined area 110 and to send the alert to one or more of those devices.

Alerts can include, but are not limited to, a text message, a phone call, an email, a voice message, or an alarm installed at the first location, and the like. In one embodiment, the alert can include a location of abnormality, a type of abnormality, a recommended solution for the abnormality, a visual explanation, and the like. In one embodiment, the visual information is displayed on a display screen of the electronic device.

In another implementation, the processor 104 is further configured to communicate an instruction to a suitably configured medical device equipment, such as medical equipment 116, present in the first location of the defined area 110 to prevent an action or a malfunction of the medical equipment. In one embodiment, the instruction is communicated based on the generated localized two-dimensional or three-dimensional representation to prevent the occurrence of the undesired event in the defined area. The instruction can be communicated as a part of the action associated the first location in the defined area 110.

In one embodiment, the instruction may include stopping an operation of the medical equipment, changing procedures performed by the medical equipment, or initiating an action to prevent any mishappening or undesired event. For example, the medical equipment may be a robot performing specific functions in the defined area 110, such as a hospital environment. The medical equipment can be configured to change a position of one of its moving parts to avoid the occurrence of the abnormality. Based on the instruction, the medical equipment may also be configured to raise an alarm to notify a user, such as a health care professional or other suitable personnel, in the vicinity of the medical equipment.

In accordance with an embodiment, the processor 104 is configured to communicate visual information along with the instruction to a specified electronic device mapped to a user present in the first location or within a specified distance from the first location in the defined area 110. In one embodiment, the visual information is a visual explanation indicative of a reason of the communicated instruction.

Optionally, the visual information along with the instruction enables the user to take necessary actions to stop or prevent the abnormality. For example, a doctor that is supposed or mapped to receive an alert of abnormality at a first location in the hospital environment may be far from that location and may not be able to take necessary steps immediately to stop or prevent the abnormality. In such a situation, the processor 104 may utilize location data of registered devices located within the defined area 110 to find an electronic device of a user who may be in the vicinity of the first location. In this manner, the aspects of the disclosed embodiments enable the identification and alerting of a user closer to the first location, who may be more suited to take necessary steps immediately to stop or prevent the abnormality.

In accordance with an embodiment, instead of obtaining the plurality of images, the processor 104 is further configured to obtain a sequence of image frames of the defined area 110 from the plurality of image-capture devices 112. In other words, the processor 104 is configured to obtain the sequence of image frames of each of the plurality of different locations 114 of the defined area 110. Optionally, the sequence of image frames is obtained in real or near-real time. In such an embodiment, the processor 104 is further configured to generate, using the neural network 106, a temporal two-dimensional representation, or in some cases a three-dimensional representation, on a localized portion of at least a segment of the sequence of image frames, where the generated temporal two-dimensional representation provides a real time or a near-real time visual indication of an abnormality over a period of time in the localized portion across at least the segment of the sequence of image frames. In an example, the sequence of image frames refers to consecutive video frames.

For example, an attention map is generated on a portion of a video. Optionally, the localized portion depicting the abnormality in a given image frame of the sequence of image frames may move marginally in the subsequent image frames of the sequence of image frames as a result the temporal two-dimensional or three-dimensional representation that may change over a period of time. This enables in providing a real time or a near-real time up-to-date visual indication of the abnormality over the period of time. It is to be understood that the temporal two-dimensional representation or three-dimensional is generated using gradients computed for each image of the sequence of images similar to the gradients computed based on at least the determined extent of deviation for input image of the plurality of images, as described above.

In accordance with an embodiment, the processor 104 is further configured to locate, using a recurrent neural network component of the neural network 106, a specific area at a given location within the defined area 110 as a point of the abnormality, based on the generated temporal two-dimensional representation or three-dimensional on the localized portion that corresponds to the specific area at the given location. Optionally, the processor 104 is configured to determine coordinates of the aforesaid specific area.

As an example, in a hospital environment, the processor 104 locates a specific area or object as a point of the abnormality in the input image of the MRI room. The point of the abnormality enables in accurately identifying a precise area of abnormality in the first location of the defined area 110.

In accordance with an embodiment, the processor 104 is further configured to identify, using the trained neural network 106, an abnormality in a medical scan image obtained from a medical imaging device of the plurality of medical imaging devices (e.g. the plurality of medical imaging devices 118) that are communicatively coupled to the processor 104. In such a case, the neural network 106 is further trained using a plurality of medical scan images obtained previously from the plurality of medical imaging device 118. Examples of the plurality of medical imaging device 118 include, but are not limited to X-ray radiography devices, MRI devices, CT scan device, or other imaging devices and the like.

Optionally, the processor 104 is configured to determine the abnormality in the medical scan images and the further identify a cause (such a disease) resulting in the abnormality in the medical scan images. The processor 104 can be further configured to utilize information about diseases and the corresponding abnormality in the medical scan images to infer the cause of the abnormality.

Figure 2:
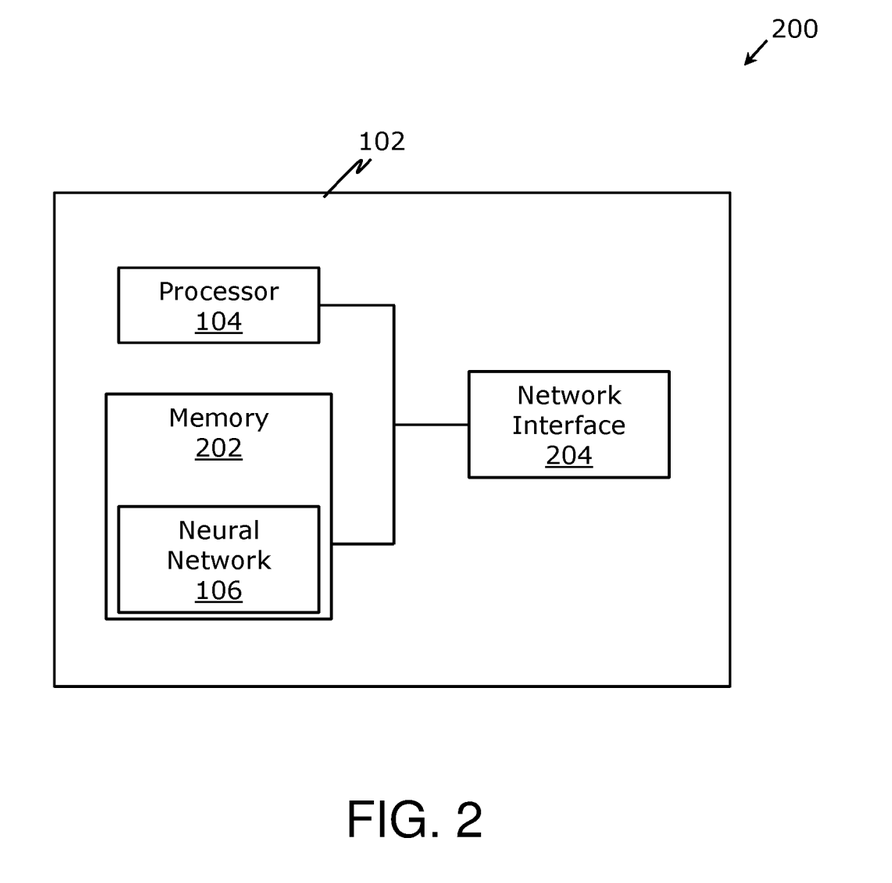
FIG. 2 is a block diagram of exemplary components of a server for abnormality detection within a defined area, in accordance with the aspects of the disclosed embodiments.

FIG. 2 is a block diagram 200 of exemplary components of a server for abnormality detection within a defined area, in accordance with the aspects of the disclosed embodiments. FIG. 2 is described in conjunction with elements from FIG. 1. With reference to FIG. 2, there is shown the server 102. The server 102 includes a memory 202, a network interface 204, the processor 104, and the neural network 106. The processor 104 is communicatively coupled to the memory 202, the network interface 204, and the neural network 106.

The memory 202 may comprise suitable logic, circuitry, interfaces, and/or code that may be configured to store instructions executable by the processor 104. The memory 202 is further configured to store the plurality of images of the defined physical area 110. The memory 202 may be further configured to store operating systems and associated applications of the server 102 including the neural network 106. Examples of implementation of the memory 202 may include, but are not limited to, Random Access Memory (RAM), Read Only Memory (ROM), Hard Disk Drive (HDD), Flash memory, and/or a Secure Digital (SD) card. A computer readable storage medium for providing a non-transient memory may include, but is not limited to, an electronic storage device, a magnetic storage device, an optical storage device, an electromagnetic storage device, a semiconductor storage device, or any suitable combination of the foregoing.

The network interface 204 includes suitable logic, circuitry, and/or interfaces that is configured to communicate with one or more external devices, such as the plurality of image-capture devices 112, the plurality of medical equipment 116, or an electronic device (such as a smartphone). Examples of the network interface 204 may include, but is not limited to, a radio frequency (RF) transceiver, an antenna, a telematics unit, one or more amplifiers, one or more oscillators, a digital signal processor, a coder-decoder (CODEC) chipset, and/or a subscriber identity module (SIM) card. Optionally, the network interface 204 may communicate by use of various wired or wireless communication protocols.

Figure 3A:
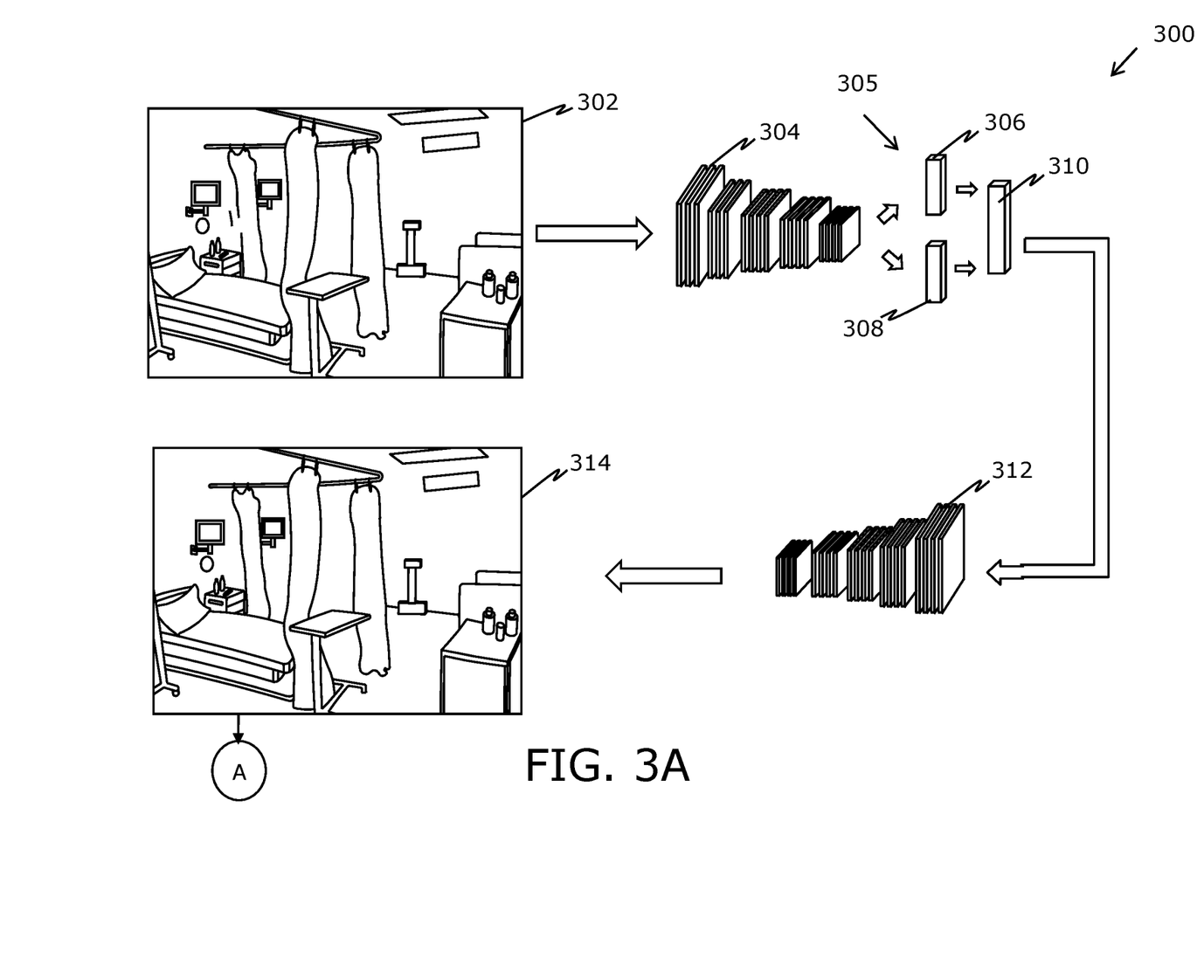
FIGS. 3A and 3B are illustrations of an exemplary scenario for implementation of a system for abnormality detection within a defined area, in accordance with the aspects of the disclosed embodiments.
Figure 3B:
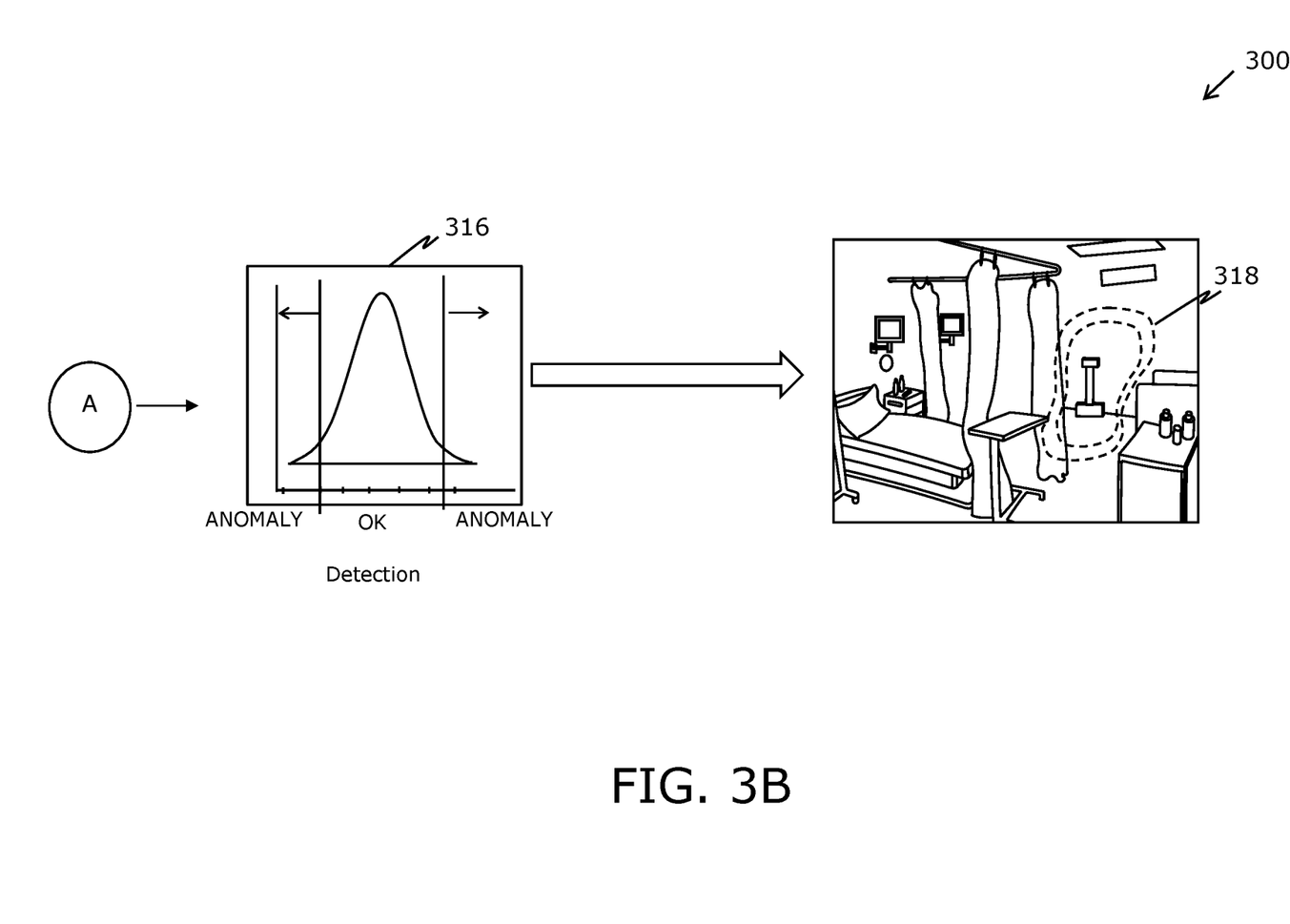

FIGS. 3A and 3B are illustration of an exemplary scenario for implementation of a system for abnormality detection within a defined area, in accordance with the aspects of the disclosed embodiments. FIGS. 3A and 3B are described in conjunction with elements from FIGS. 1 and 2.

With reference to FIGS. 3A and 3B, there is shown an exemplary scenario 300. In FIG. 3A, there is shown an input image 302 of a hospital environment received by an encoder 304 of the trained neural network 106, for example a variational autoencoder. The encoder 304 is configured to generate products 305 from an inference of the input image 302. In one embodiment, these products 305 can include, but are not limited to a mean vector 306 and a standard deviation vector 308.

The encoder 304 is further configured to determine an extent of a deviation a probability distribution of each input image 302 of the plurality of images with respect to a referential probability distribution of one or more reference images. In one embodiment, this includes determining an extent of a deviation of the computed mean vector 306 and the standard deviation vector 308 of the input image 302 with respect to a reference mean vector and a reference standard deviation vector of a reference image. In other words, a resultant vector 310 (e.g. a sample latent vector) is derived from a difference of the computed mean vector and the standard deviation vector of the input image 302 from the reference mean vector and the reference standard deviation vector of the reference image. Further, a decoder 312 of the neural network 106 is configured to generate an output image 314 (similar the original input).

With reference to FIG. 3B, there is shown a graphical representation 316 depicting detection of abnormality in the input image 302. The processor 104, using the trained neural network 106, is configured to compute gradients by back-propagating the resultant vectors in the trained neural network 106 to compute the gradients. The computed gradients are then used to generate a localized two-dimensional or three-dimensional representation 318 (e.g. an attention map) in a specific portion of the input image 302 using the trained neural network 106. The generated localized two-dimensional or three-dimensional representation 318 provides a visual indication of an abnormality.

Figure 4:
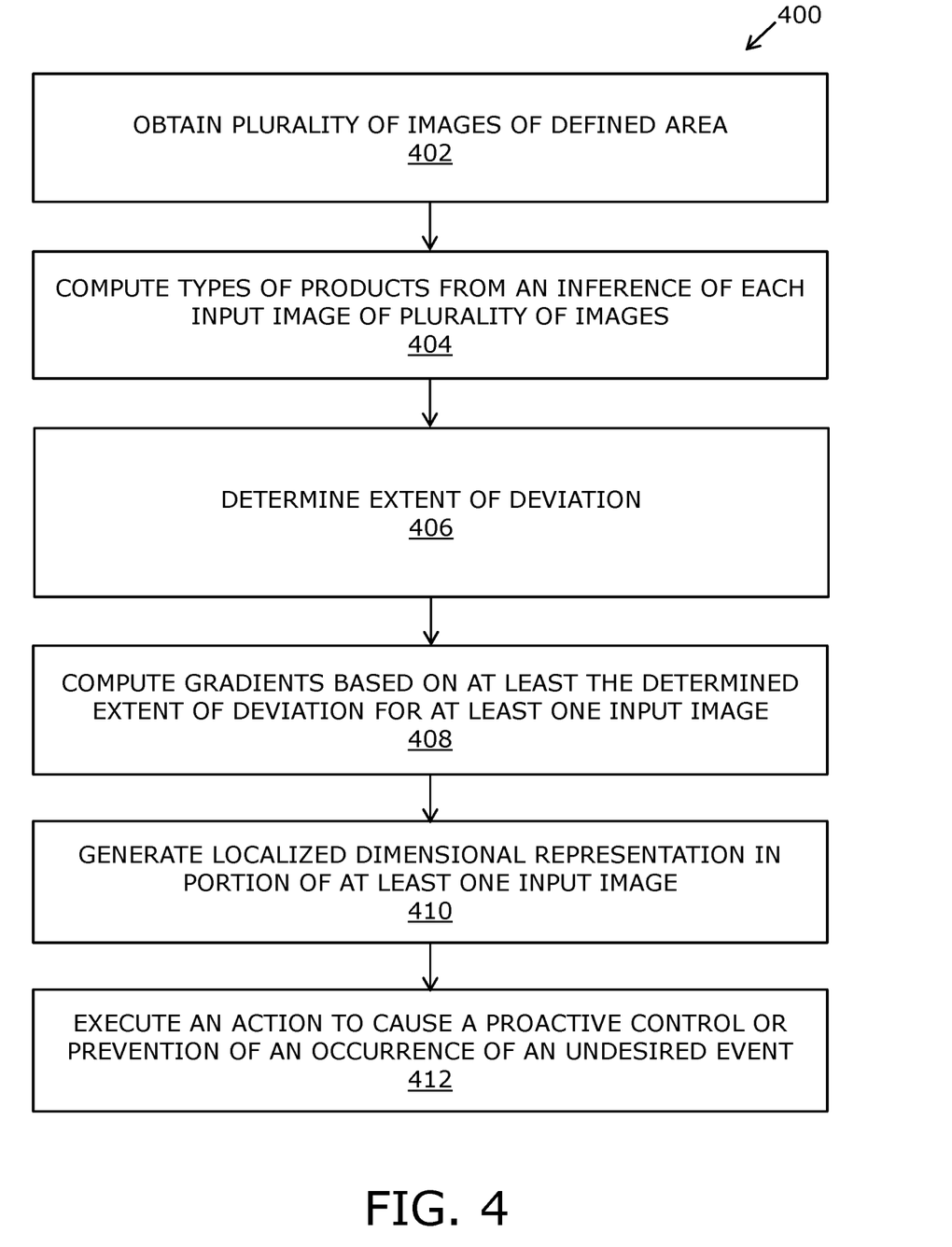
FIG. 4 is a flowchart of an exemplary method for abnormality detection within a defined area, in accordance with the aspects of the disclosed embodiments.

FIG. 4 is a flowchart of an exemplary method for abnormality detection within a defined area, in accordance with the aspects of the disclosed embodiments. FIG. 4 is described in conjunction with elements from FIGS. 1, 2, 3A, and 3B.

With reference to FIG. 4 there is shown a flowchart 400. At step 402, a plurality of images of the defined area is obtained by the processor 104 from the one or more image-capture devices. At step 404, one or more types of products from an inference of each input image of the plurality of images is computed by the processor 104 using the trained neural network 106. The plurality of images is associated with a plurality of different locations in the defined physical area 110. At step 406, an extent of deviation of properties of a probability distribution of each input image of the plurality of images with respect to a referential probability distribution of one or more reference images is determined by the processor 104 using the trained neural network 106. At step 408, gradients associated with the trained neural network 106 are computed, by the processor 104, using the trained neural network 106, based on at least the determined extent of deviation for at least one input image of the plurality of images when the determined extent of deviation for the at least one input image is greater than a defined threshold. At step 410, a localized two-dimensional or three-dimensional representation is generated in a portion of the at least one input image associated with a first location of the plurality of locations, based on the computed gradients, by the processor 104 using the trained neural network 106. The generated localized two-dimensional or three-dimensional representation provides a visual indication of an abnormality located in the first location within the defined area 110.

At step 412, an action associated the first location in the defined physical area 110 is executed by the processor 104, based on the generated localized representation. The executed action causes an action, such as a proactive control or prevention of an occurrence of an undesired event in the defined area 110.

Various embodiments and variants disclosed above, with respect to the aforementioned system 100, apply mutatis mutandis to the method. The method described herein is computationally efficient and does not cause processing burden on the processor 104.

Figure 5A:
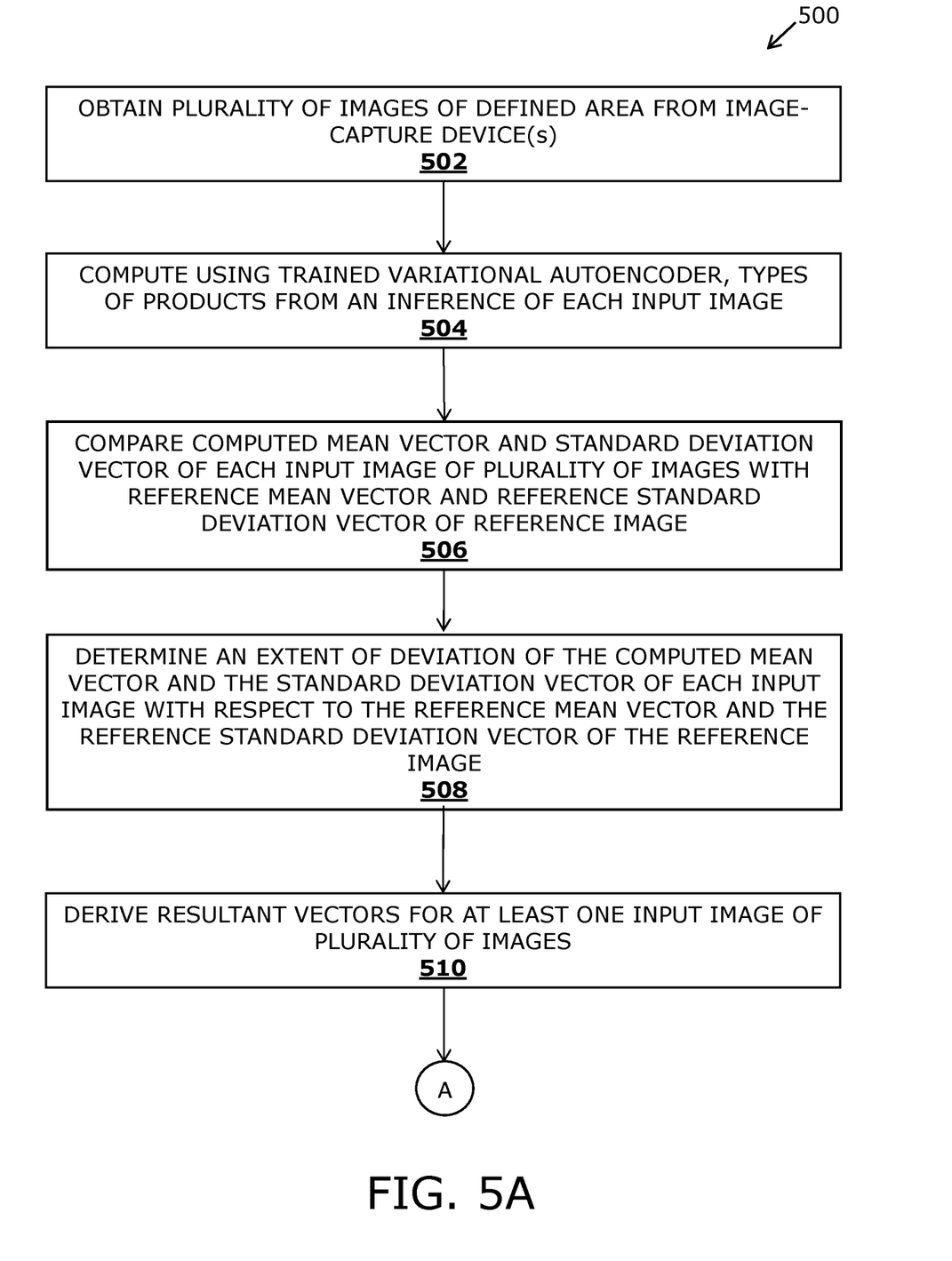
FIGS. 5A-5C are flowcharts of an exemplary method for abnormality detection within a defined area, in accordance with another aspect of the disclosed embodiments.
Figure 5B:
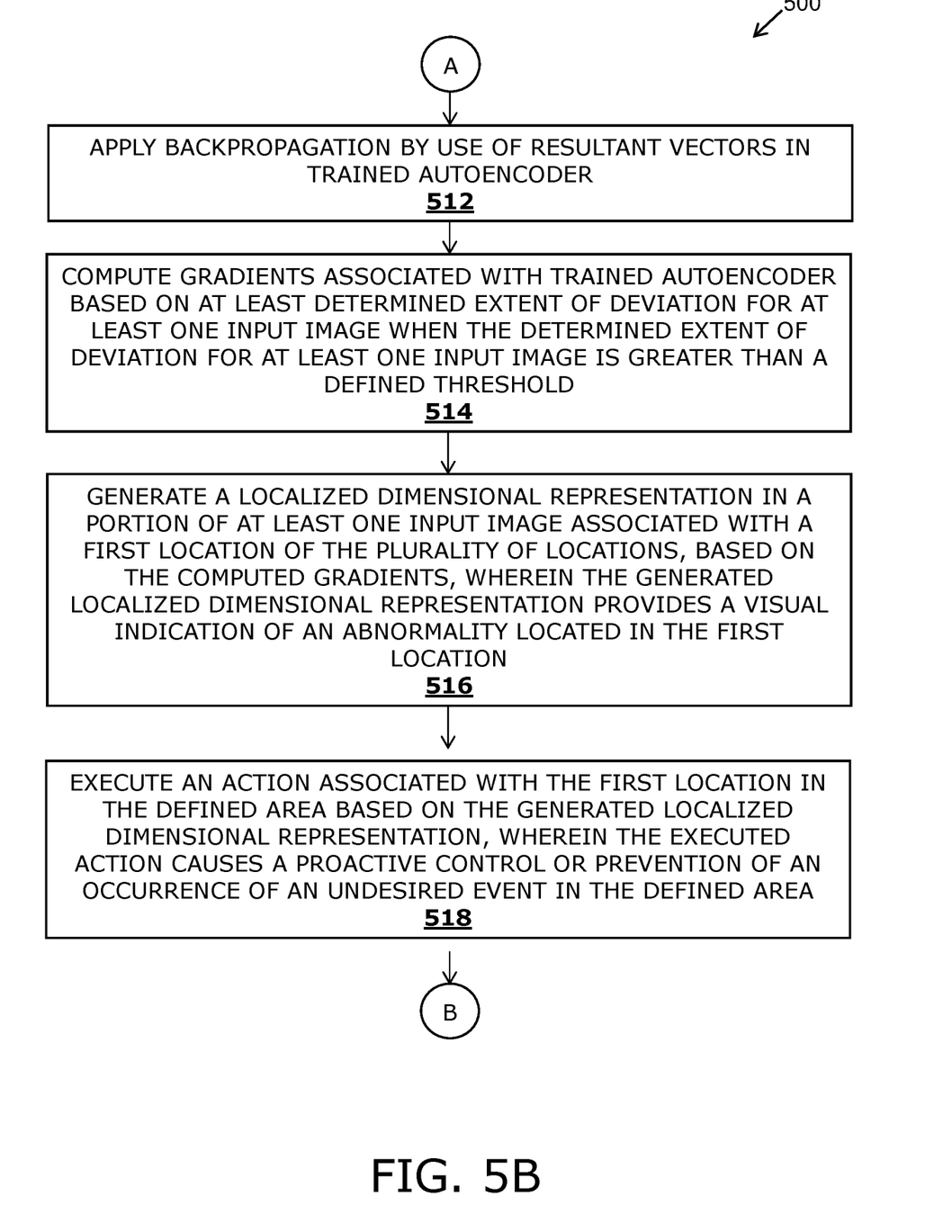
Figure 5C:
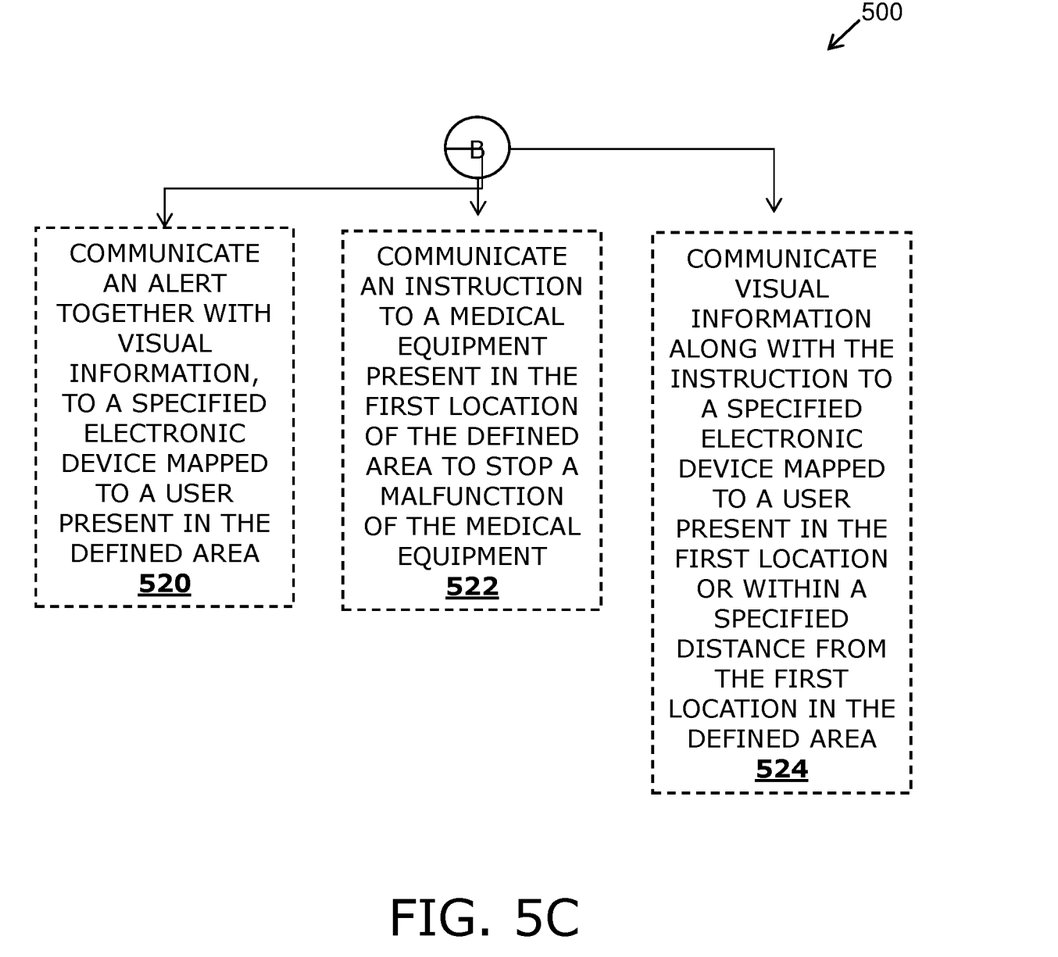

FIGS. 5A-5C illustrate a flowchart 500 of a method for abnormality detection within a defined area, in accordance with another aspect of the disclosed embodiments. At step 502, a plurality of images of the defined area is obtained by a processor from the one or more image-capture devices 112. Alternatively, a sequence of image frames of the defined area 110 is received by the processor 104 from the one or more image-capture devices 112.

At step 504, one or more types of products from an inference of each input image of the plurality of images is computed by the processor 104 using a trained neural network 106. The plurality of images is associated with a plurality of different locations 114 in the physical area 110.

At step 506, the one or more types of products from an inference with the each input image, such as the computed mean vector and the standard deviation vector of each input image of the plurality of images, is compared with a reference, such as a reference mean vector and a reference standard deviation vector of a corresponding reference image. At step 508, an extent of deviation of properties of a probability distribution of each input image of the plurality of images with respect to a referential probability distribution of one or more reference images is determined. In this example, this includes determining an extent of deviation of the computed mean vector and the standard deviation vector of each input image of the plurality of images with respect to the reference mean vector and the reference standard deviation vector of a reference image.

At step 510, resultant vectors for the at least one input image of the plurality of images are derived. The resultant vectors are derived from a difference of the computed mean vector and the standard deviation vector of the at least one input image from the reference mean vector and the reference standard deviation vector. At step 512, backpropagation is applied by use of the resultant vectors in the trained neural network 106.

At step 514, gradients associated with the trained neural network 106 are computed, by the processor 104, using the trained neural network 106, based on at least the determined extent of deviation for at least one input image of the plurality of images when the determined extent of deviation for the at least one input image is greater than a defined threshold. At step 516, a localized dimensional representation, such as a two-dimensional or three-dimensional representation, is generated using the trained neural network 106 in a portion of the at least one input image associated with a first location of the plurality of different locations 114, based on the computed gradients. The generated localized representation provides a visual indication of an abnormality located in the first location within the defined area 110.

At step 518, an action associated the first location in the defined area 110 is executed based on the generated localized representation. The executed action can include an action to cause a proactive control or prevention of an occurrence of an undesired event in the defined area 110. The executed action may include communicating instructions and/or information for controlling or preventing occurrence of an undesired event.

At step 520, an alert together with visual information is communicated, to a specified electronic device mapped to a user associated with or present in the defined area. The alert is communicated based on the generated localized representation to indicate the abnormality located in the first location within the defined area 110. The visual information is a visual explanation indicative of a reason of the alert. The alert together with visual information is communicated as a part of the action associated the first location in the defined area 110.

In another example, at step 522, an instruction is communicated to medical equipment present in the first location of the defined area 110 to stop an action or malfunction of the medical equipment (such as the medical equipment 116). The instruction is communicated based on the generated localized dimensional representation to prevent the occurrence of the undesired event in the defined area 110. The instruction is communicated as a part of the action associated the first location in the defined area 110.

In yet another example, at step 524, an instruction is communicated to the medical equipment present in the first location of the defined area 110 to stop an action or malfunction of the medical equipment. The instruction is communicated based on the generated localized dimensional representation to prevent the occurrence of the undesired event in the defined area 110. The instruction is communicated as a part of the action associated the first location in the defined physical area 110.

Modifications to embodiments of the aspects of the disclosed embodiments described in the foregoing are possible without departing from the scope of the aspects of the disclosed embodiments as defined by the accompanying claims. Expressions such as "including", "comprising", "incorporating", "have", "is" used to describe and claim the aspects of the disclosed embodiments are intended to be construed in a non-exclusive manner, namely allowing for items, components or elements not explicitly described also to be present.

Reference to the singular is also to be construed to relate to the plural.

Thus, while there have been shown, described and pointed out, fundamental novel features of the invention as applied to the exemplary embodiments thereof, it will be understood that various omissions, substitutions and changes in the form and details of devices and methods illustrated, and in their operation, may be made by those skilled in the art without departing from the spirit and scope of the presently disclosed invention. Further, it is expressly intended that all combinations of those elements, which perform substantially the same function in substantially the same way to achieve the same results, are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for abnormality detection within a defined physical area, comprising:
obtaining, by a processor, a plurality of images of the defined area from one or more image capture devices;
computing, by the processor using a trained neural network, one or more types of products from an inference with each input image of the plurality of images, wherein the plurality of images are associated with a plurality of different locations in the defined area;
determining, by the processor using the trained neural network, an extent of deviation of properties of a probability distribution of each input image of the plurality of images with respect to a referential probability distribution of one or more reference images;
computing by the processor using the trained neural network, gradients associated with the trained neural network based on at least the determined extent of deviation for at least one input image of the plurality of images when the determined extent of deviation for the at least one input image is greater than a defined threshold;
generating, by the processor using the trained neural network, a localized two-dimensional or three-dimensional representation in a portion of the at least one input image associated with a first location of the plurality of locations, based on the computed gradients, wherein the generated localized two-dimensional or three-dimensional representation provides a visual indication of an abnormality located in the first location within the defined area; and
executing, by the processor, an action associated with the first location in the defined area based on the generated localized two-dimensional or three-dimensional representation, wherein the executed action is configured to cause a proactive control of an occurrence of an undesired event in the defined area.

2. The method according to claim 1, wherein the one or more types of products from an inference include a mean vector and a standard deviation vector, and the method further comprises comparing, by the processor, the mean vector and the standard deviation vector of each input image of the plurality of images with a reference mean vector and a reference standard deviation vector of the corresponding reference image to determine the extent of deviation.

3. The method according to claim 1, further comprising deriving, by the processor using the trained neural network, resultant vectors for the at least one input image of the plurality of images, wherein the resultant vectors are derived from a difference of a computed mean vector and a standard deviation vector of the at least one input image from a reference mean vector and a reference standard deviation vector.

4. The method according to claim 3, further comprising applying, by the processor, backpropagation by use of the resultant vectors in the trained neural network to compute the gradients.

5. The method according to claim 1, further comprising communicating, by the processor, an alert together with visual information, to a specified electronic device mapped to a user present in the defined area, wherein the alert is communicated based on the generated localized two-dimensional or three-dimensional representation to indicate the abnormality located in the first location within the defined area, and wherein the visual information is a visual explanation indicative of a reason of the alert, and wherein the alert together with visual information is communicated as a part of the action associated the first location in the defined area.

6. The method according to claim 1, further comprising communicating, by the processor, an instruction to a medical equipment present in the first location of the defined area to stop an action or malfunction of the medical equipment, wherein the instruction is communicated based on the generated localized two-dimensional or three-dimensional representation to prevent the occurrence of the undesired event in the defined area, and wherein the instruction is communicated as a part of the action associated the first location in the defined area.

7. The method according to claim 6, further comprising communicating, by the processor, visual information along with the instruction to a specified electronic device mapped to a user present in the first location or within a specified distance from the first location in the defined area, wherein the visual information is a visual explanation indicative of a reason of the communicated instruction.

8. The method according to claim 1, further comprising obtaining, by the processor, a sequence of image frames of the defined area from the one or more image-capture devices.

9. The method according to claim 8, further comprising generating, by the processor using the neural network, a temporal two-dimensional or three-dimensional representation on a localized portion across at least a segment of the sequence of image frames, wherein the generated temporal two-dimensional representation provides a real time or a near-real time visual indication of an abnormality over a period of time in the localized portion across at least the segment of the sequence of image frames.

10. The method according to claim 9, further comprising locating, by the processor using a recurrent neural network component of the neural network, a specific area at a given location within the defined area as a point of the abnormality, based on the generated temporal two-dimensional or three-dimensional representation on the localized portion that corresponds to the specific area at the given location.

11. The method according to claim 1, further comprising executing, by the processor, an unsupervised or a semi-supervised training of an neural network using training data of images of the defined area to obtain the trained neural network.

12. The method according to claim 1, wherein the trained neural network is an attention-based variational autoencoder, and wherein the defined area is a hospital environment.

13. The method according to claim 1, further comprising identifying, by the processor using the trained neural network, an abnormality in a medical scan image obtained from a medical imaging device of a plurality of medical imaging devices that are communicatively coupled to the processor, wherein the trained neural network is further trained using a plurality of medical scan images obtained previously from the plurality of medical imaging devices.

14. A system for abnormality detection within a defined area, the system comprising:
a server that includes a processor configured to:
obtain a plurality of images of the defined area from one or more image-capture devices;
compute, using a trained neural network, one or more types of products from an inference with each input image of the plurality of images, wherein the plurality of images are associated with a plurality of different locations in the defined area;

determine, using the trained neural network, an extent of deviation properties of a probability distribution of each input image of the plurality of images with respect to a referential probability distribution of one or more reference images;

compute, using the trained neural network, gradients associated with the trained neural network based on at least the determined extent of deviation for at least one input image of the plurality of images when the determined extent of deviation for the at least one input image is greater than a defined threshold;

generate, using the trained neural network, a localized dimensional representation in a portion of the at least one input image associated with a first location of the plurality of locations, based on the computed gradients, wherein the generated localized dimensional representation provides a visual indication of an abnormality located in the first location within the defined area; and execute an action associated the first location in the defined area based on the generated localized dimensional representation, wherein the executed action is configured to cause a proactive control or prevention of an occurrence of an undesired event in the defined area.

15. The system according to claim 14, wherein the one or more types of products from the inference include a computed mean vector and a standard deviation vector and the processor is further configured to compare the computed mean vector and the standard deviation vector of each input image of the plurality of images with a reference mean vector and a reference standard deviation vector of a corresponding reference image to determine the extent of deviation.

16. The system according to claim 15, wherein the processor is further configured to derive, using the trained neural network, resultant vectors for the at least one input image of the plurality of images, wherein the resultant vectors are derived from a difference of the computed mean vector and the standard deviation vector of the at least one input image from the reference mean vector and the reference standard deviation vector.

17. The system according to claim 16, wherein the processor is further configured to apply backpropagation by use of the resultant vectors in the trained neural network to compute the gradients.

18. The system according to claim 14, wherein the processor is further configured to obtain a sequence of image frames of the defined area from the one or more image-capture devices.

19. The system according to claim 18, wherein the processor is further configured to generate, using the neural network, a temporal dimensional representation on a localized portion of at least a segment of the sequence of image frames, wherein the generated temporal dimensional representation provides a real time or a near-real time visual indication of an abnormality over a period of time in the localized portion across at least the segment of the sequence of image frames.

20. A non-transitory computer-readable medium having stored thereon, computer implemented instructions that when executed by a computer causes the computer to execute operations, the operations comprising:

obtaining a plurality of images of the defined physical area from one or more image-capture devices;

computing, using a trained neural network, one or more types of products from an inference of each input image of the plurality of images, wherein the plurality of images are associated with a plurality of different locations in the defined area;

determining, using the trained neural network, an extent of deviation of properties of a probability distribution of each input image of the plurality of images with respect to a referential probability distribution of one or more reference images;

computing, using the trained neural network, gradients associated with the trained neural network based on at least the determined extent of deviation for at least one input image of the plurality of images when the determined extent of deviation for the at least one input image is greater than a defined threshold;

generating, using the trained neural network, a localized dimensional representation in a portion of the at least one input image associated with a first location of the plurality of locations, based on the computed gradients, wherein the generated localized two-dimensional representation provides a visual indication of an abnormality located in the first location within the defined area; and executing an action associated the first location in the defined area based on the generated localized dimensional representation, wherein the executed action is configured to cause a proactive control or prevention of an occurrence of an undesired event in the defined area.

* * * * *